United States Patent
Kim et al.

(10) Patent No.: US 11,286,229 B2
(45) Date of Patent: Mar. 29, 2022

(54) METHOD OF PREPARING ESTER-BASED COMPOSITION

(71) Applicant: LG CHEM, LTD., Seoul (KR)

(72) Inventors: Hyun Kyu Kim, Daejeon (KR); Jeong Ju Moon, Daejeon (KR); Joo Ho Kim, Daejeon (KR); Mi Yeon Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 860 days.

(21) Appl. No.: 16/077,954

(22) PCT Filed: Oct. 30, 2017

(86) PCT No.: PCT/KR2017/012070
§ 371 (c)(1),
(2) Date: Aug. 14, 2018

(87) PCT Pub. No.: WO2018/084513
PCT Pub. Date: May 11, 2018

(65) Prior Publication Data
US 2021/0179530 A1    Jun. 17, 2021

(30) Foreign Application Priority Data
Nov. 1, 2016    (KR) ................. 10-2016-0144514

(51) Int. Cl.
*C07C 67/10*    (2006.01)
*C08K 5/101*    (2006.01)

(52) U.S. Cl.
CPC .............. *C07C 67/10* (2013.01); *C08K 5/101* (2013.01)

(58) Field of Classification Search
CPC ..................... C07C 67/10; C08K 5/101
USPC ............................................. 560/78
See application file for complete search history.

(56) References Cited

U.S. PATENT DOCUMENTS

| | | | |
|---|---|---|---|
| 4,252,738 | A | 2/1981 | Hartmann et al. |
| 4,675,434 | A | 6/1987 | Uhm et al. |
| 6,310,235 | B1 | 10/2001 | Gick |
| 7,205,349 | B2 | 4/2007 | Koch et al. |
| 2004/0138358 | A1 | 7/2004 | Koch et al. |
| 2008/0058450 | A1 | 3/2008 | Stimpson et al. |
| 2011/0275808 | A1 | 11/2011 | Reeves et al. |
| 2012/0136101 | A1 | 5/2012 | Hong et al. |
| 2016/0264509 | A1 | 9/2016 | Kaller et al. |
| 2017/0081501 | A1 | 3/2017 | Kim et al. |

(Continued)

FOREIGN PATENT DOCUMENTS

| | | |
|---|---|---|
| CN | 1257472 A | 6/2000 |
| CN | 1563159 A | 1/2005 |
| CN | 102993595 A | 3/2013 |

(Continued)

*Primary Examiner* — Deborah D Carr
(74) *Attorney, Agent, or Firm* — Dentons US LLP

(57) ABSTRACT

The present invention relates to a method of preparing an ester-based composition, which includes mixing a dibenzoic acid and a carboxylic acid to prepare an acid mixture and reacting the acid mixture with an alcohol, wherein a product of the reaction includes a benzoic acid ester-based material and a carboxylic acid ester-based material. The preparation method can improve a reaction rate and a temperature rising rate, and can also reduce energy, by adding a carboxylic acid and/or a carboxylic acid ester-based material in a preparation process.

5 Claims, 2 Drawing Sheets

(56) References Cited

U.S. PATENT DOCUMENTS

2018/0134870 A1    5/2018   Tiyapiboonchaiya et al.

FOREIGN PATENT DOCUMENTS

| | | | |
|---|---|---|---|
| CN | 105683147 A | 6/2016 | |
| JP | 63-127437 A | 11/1978 | |
| JP | 60-4151 A | 1/1985 | |
| JP | 60-172945 A | 9/1985 | |
| JP | 63-57550 A | 3/1988 | |
| JP | 2004-114559 A | 4/2004 | |
| JP | 2004-143177 A | 5/2004 | |
| JP | 2011-520794 A | 7/2011 | |
| JP | 2013049861 A | 3/2013 | |
| JP | 2015-504950 A | 2/2015 | |
| JP | 5715105 B2 | 5/2015 | |
| KR | 10-2016-0079065 A | 7/2016 | |
| KR | 1020160079065 A * | 7/2016 | |
| KR | 10-2016-0099453 A | 8/2016 | |
| KR | 10-1663586 B1 | 10/2016 | |
| KR | 10-1742923 B1 | 6/2017 | |
| TW | 201533017 A | 9/2015 | |
| TW | 201634438 A | 10/2016 | |
| WO | 2008/010578 A1 | 1/2008 | |
| WO | 2009062356 A1 | 5/2009 | |
| WO | 2015/063189 A1 | 5/2015 | |
| WO | WO-2015063189 A1 * | 5/2015 | ............ C07C 67/08 |
| WO | 2015/119443 A1 | 8/2015 | |
| WO | 2017/003388 A1 | 1/2017 | |

* cited by examiner

METHOD OF PREPARING ESTER-BASED COMPOSITION

CROSS-REFERENCE TO RELATED APPLICATION

This application is a National Stage Application of International Application No. PCT/KR2017/012070 filed Oct. 30, 2017, and claims the benefit of Korean Patent Application No. 10-2016-0144514 filed Nov. 1, 2016, all of which are hereby incorporated by reference in their entirety for all purposes as if fully set forth herein.

TECHNICAL FIELD

The present invention relates to a method of preparing an ester-based composition which improves a reaction rate and a temperature rising rate, and also reduces energy.

BACKGROUND ART

Conventionally, a plasticizer forms an ester through a reaction between an alcohol and a polycarboxylic acid such as phthalic acid or adipic acid. In addition, in consideration of domestic and international regulations for phthalate-based plasticizers harmful to humans, there is ongoing research on plasticizer compositions that can replace phthalate-based plasticizers such as terephthalate-, trimellitate-, and other polymer-based plasticizers.

Generally, a plasticizer is used as a material for various products such as electric wires, pipes, flooring materials, wallpaper, sheets, artificial leather, tarpaulins, tape and food wrapping materials obtained in the related industries according to a processing method such as extrusion molding, injection molding or calendering after suitably adding various additives including resins such as polyvinyl chloride (PVC) and the like, fillers, stabilizers, pigments, anti-fogging agents, and the like to provide various processing properties.

In the current plasticizer market, environmentally-friendly plasticizers are competitively developing in the related field due to environmental issues of phthalate plasticizers, and recently, new products for overcoming the inferiority of di(2-ethylhexyl)terephthalate (DEHTP), which are being used as general purpose products among such environmentally-friendly plasticizers, in qualities such as plasticization efficiency, migration ability, and the like have been developed.

DISCLOSURE

Technical Problem

The present invention is designed to solve the problem as described above, and it is an aspect of the present invention to provide a method of preparing an ester-based composition which can improve a reaction rate and a temperature rising rate, and can also reduce energy by adding a carboxylic acid and/or a carboxylic acid ester-based material in a preparation process.

Technical Solution

In order to accomplish the above objectives, according to one embodiment of the present invention, there is provided a method of preparing an ester-based composition, which includes reacting a) a dibenzoic acid represented by Chemical Formula 1 below; b) one or more selected from the group consisting of a carboxylic acid represented by Chemical Formula 2 below and a carboxylic acid ester-based material including one or more compounds represented by Chemical Formula 5 below; and c) an alcohol including one or more compounds represented by Chemical Formula 3 below.

A product of the reaction includes a benzoic acid ester-based material including one or more compounds represented by Chemical Formula 4 below and a carboxylic acid ester-based material including one or more compounds represented by Chemical Formula 5 below.

[Chemical Formula 1]

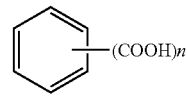

In Chemical Formula 1, n is 2.

[Chemical Formula 2]

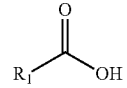

In Chemical Formula 2, $R_1$ is a C1 or C2 alkyl group.

$$R_2—OH \quad \text{[Chemical Formula 3]}$$

In Chemical Formula 3, $R_2$ is a C1 to C12 linear alkyl group or a C3 to C12 branched alkyl group.

[Chemical Formula 4]

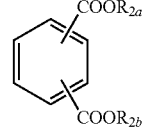

In Chemical Formula 4, $R_{2a}$ and $R_{2b}$ are the same or different from each other, and each independently are a linear alkyl group or a C3 to C12 branched alkyl group.

[Chemical Formula 5]

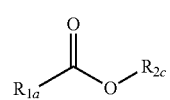

In Chemical Formula 5, $R_{1a}$ is a C1 or C2 alkyl group, and $R_2$ is a C1 to C12 linear alkyl group or a C3 to C12 branched alkyl group.

Advantageous Effects

A method of preparing an ester-based composition according to an embodiment of the present invention is applied in the preparation of a plasticizer composition, and can improve a reaction rate and a temperature rising rate, and can also reduce energy, by adding a carboxylic acid and/or a carboxylic acid ester-based material in a preparation process.

MODE FOR INVENTION

Figure 1:
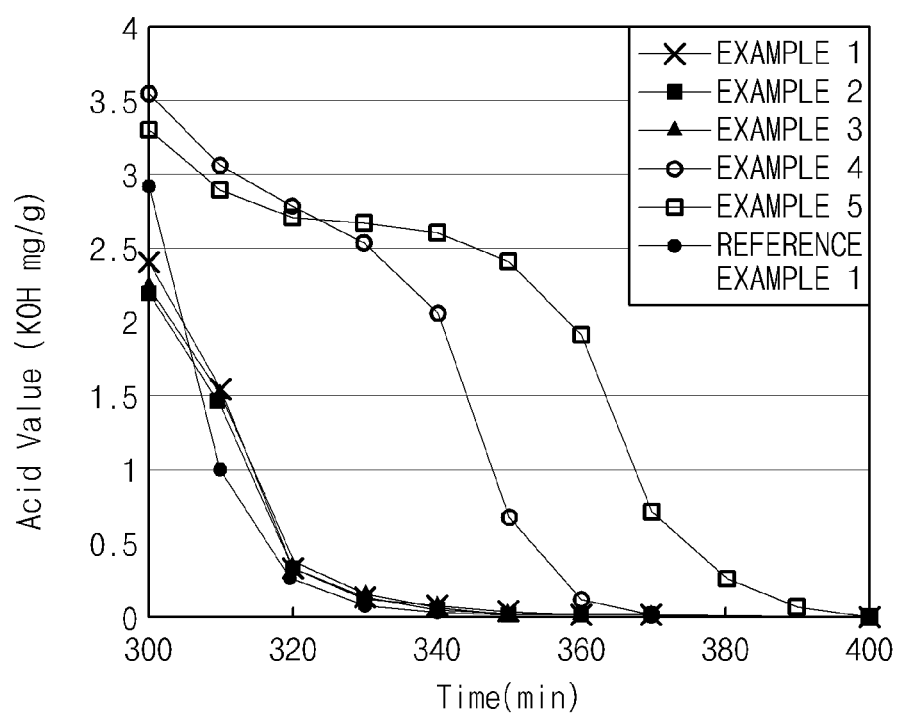
FIG. 1 is a graph obtained by measuring a reaction rate of esterification.

Hereinafter, the present invention will be described in further detail to help in understanding the present invention. Terms and words used in this specification and claims should not be interpreted as limited to commonly used meanings or meanings in dictionaries and should be interpreted with meanings and concepts which are consistent with the technological scope of the invention based on the principle that the inventors have appropriately defined concepts of terms in order to describe the invention in the best way.

According to an embodiment of the present invention, there is provided a method of preparing an ester-based composition, which includes preparing and reacting a dibenzoic acid represented by Chemical Formula 1 below, a carboxylic acid represented by Chemical Formula 2 below, and an alcohol including one or more compounds represented by Chemical Formula 3 below.

In addition, a product of the reaction includes a benzoic acid ester-based material including one or more compounds represented by Chemical Formula 4 below and a carboxylic acid ester-based material including one or more compounds represented by Chemical Formula 5 below.

Reactants and Products

Chemical Formulas 1 to 5 representing compounds that are involved in the reaction and compounds included in a product of the reaction are specifically as follows.

As one of materials that are involved in the reaction, a dibenzoic acid may be a compound represented by Chemical Formula 1 below.

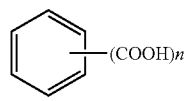

[Chemical Formula 1]

In Chemical Formula 1, n is 2.

Chemical Formula 1 represents a dibenzoic acid-based material in which two carboxyl groups are attached to a benzene ring. For example, phthalic acid, isophthalic acid, or terephthalic acid may be used as the dibenzoic acid-based material, and preferably, terephthalic acid is used.

In addition, as a material that is mixed with the dibenzoic acid to form an acid mixture, a carboxylic acid may be used. The carboxylic acid may be represented by Chemical Formula 2 below.

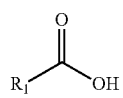

[Chemical Formula 2]

In Chemical Formula 2, $R_1$ is a C1 or C2 alkyl group.

For example, acetic acid or propionic acid may be used as the carboxylic acid, and preferably, acetic acid is used.

An alcohol that is esterified with the acid mixture of the dibenzoic acid and the carboxylic acid may include one or more compounds represented by Chemical Formula 3 below.

[Chemical Formula 3]

In Chemical Formula 3, $R_2$ is a C1 to C12 linear alkyl group or a C3 to C12 branched alkyl group.

The compound represented by Chemical Formula 3 may be a linear or branched primary alcohol. In some cases, only one type or two or more types of alcohol that is/are involved in esterification may be used, and preferably, one type or two types of alcohol is/are used. Also, $R_2$ preferably is a C4 to C10 linear or branched alkyl group.

Materials prepared by reacting the acid mixture with the alcohol are ester-based compounds which are a result of esterification, and may be represented by Chemical Formulas 4 and 5 below.

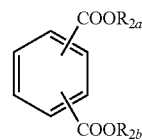

[Chemical Formula 4]

In Chemical Formula 4, $R_{2a}$ and $R_{2b}$ are the same or different from each other, and each independently are a linear alkyl group or a C3 to C12 branched alkyl group.

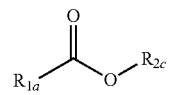

[Chemical Formula 5]

In Chemical Formula 5, $R_{ia}$ is a C1 or C2 alkyl group, and $R_{2c}$ is a C1 to C12 linear alkyl group or a C3 to C12 branched alkyl group.

A dibenzoic acid ester-based material including the compound represented by Chemical Formula 4 may be produced by the reaction between the dibenzoic acid and the alcohol, and a carboxylic acid ester-based material including the compound represented by Chemical Formula 5 may be produced by the reaction between the carboxylic acid and the alcohol.

Accordingly, $R_{2a}$ to $R_{2c}$ in Chemical Formulas 4 and 5 may be derived from $R_2$ in the compound represented by Chemical Formula 3, and may be alkyl groups with the same carbon number. Also, when two or more compounds represented by Chemical Formula 3 are used as the alcohol, $R_{2a}$ and $R_{2b}$ in Chemical Formula 4 may be different from each other, and a dibenzoic acid ester-based material including two or more compounds represented by Chemical Formula 4 may be produced. For the carboxylic acid ester-based material represented by Chemical Formula 5, the same reaction may also occur.

Specifically, the compound represented by Chemical Formula 4 may be, for example, an isophthalate, a terephthalate, or a phthalate, and preferably is a terephthalate. Also, the dibenzoic acid ester-based material including the compound represented by Chemical Formula 4 may be, for example, a single compound or a mixture in which two or more compounds are mixed. When the dibenzoic acid ester-based material is a single compound in which only one alcohol is used, $R_{2a}$ and $R_{2b}$ may be the same, and preferably are a butyl group, an isobutyl group, an octyl group, a 2-ethylhexyl group, an isononyl group, a 2-propylheptyl group, or an isodecyl group.

In addition, when two or more alcohols are used, $R_{2a}$ and $R_{2b}$ may be the same or different from each other, and a dibenzoic acid ester-based material may be produced as a mixture of two or more compounds. In this case, an alkyl group to be applied may be as described above.

The compound represented by Chemical Formula 5 may also be produced in the same manner as the compound represented by Chemical Formula 4, and alkyl groups exemplified by $R_{2a}$ and $R_{2b}$ may also be applied to $R_{2c}$.

Preparation Method

1) Preparation of Reactants

In the method of preparing an ester-based composition, esterification of a dibenzoic acid with an alcohol is performed, and a carboxylic acid and/or a carboxylic acid ester-based material may be added at an early stage of the reaction. In this case, the carboxylic acid may be contained in each or both of the dibenzoic acid and the alcohol, or may be separately added before or during the reaction. Also, it is sufficient if the carboxylic acid ester-based material is optionally added before or during the reaction so as to be included together with reaction raw materials and a product, and the addition method, order, the timing of the addition, or the like is not particularly limited.

For example, the dibenzoic acid and the carboxylic acid may form an acid mixture. The carboxylic acid may be included at a content of about 10 wt % or less, 5 wt % or less, 3 wt % or less, or 2 wt % or less, preferably 1 wt % or less, and more preferably 0.5 wt % or less with respect to the total weight of the acid mixture. The content of the carboxylic acid in the acid mixture may not be a factor that greatly affects the reaction, but it may be a factor that determines the content of the carboxylic acid ester-based material including the compound represented by Chemical Formula 5 in a product. Therefore, it is necessary to adjust an amount of the carboxylic acid included in the acid mixture.

In the method of preparing an ester-based composition, a reactant may be prepared through various methods. For example, a carboxylic acid ester-based material including one or more compounds represented by Chemical Formula 5 which is a product of the reaction may be added at an early stage of the reaction.

That is, a carboxylic acid ester-based material is added together when an acid mixture is formed so that the carboxylic acid ester-based material is included in a product of the reaction. Therefore, a method in which a carboxylic acid ester-based material is added in advance so as to perform a specific role may be applied.

In addition, unlike the above-described preparation method, a method in which esterification is performed not using a dibenzoic acid and a carboxylic acid but using only a dibenzoic acid by adding a carboxylic acid ester-based material to a dibenzoic acid when an acid mixture is formed so that a carboxylic acid ester-based material performs a specific role may be applied.

As described above, regardless of whether a reactant is prepared through any method, it may be sufficient if the content of a carboxylic acid ester-based material including the compound represented by Chemical Formula 5 finally included in a product of the reaction satisfies 11 parts by weight or less, preferably 8 parts by weight or less with respect to 100 parts by weight of the dibenzoic acid.

2) Esterification

After the acid mixture is formed, esterification of the acid mixture with an alcohol may be performed. The esterification is direct esterification, and may be a reaction in which an acid reacts with an alcohol to produce an ester.

The direct esterification may be performed, more specifically, by adding an acid mixture to an alcohol and then adding a catalyst to induce a reaction under a nitrogen atmosphere; removing an unreacted alcohol and neutralizing an unreacted acid; and performing dehydration and filtration through distillation under reduced pressure.

The alcohol may be used at a content of 150 to 500 mol %, 200 to 400 mol %, 200 to 350 mol %, 250 to 400 mol %, or 270 to 330 mol % with respect to 100 mol % of the acid mixture.

Meanwhile, the catalyst may be, for example, one or more selected from an acidic catalyst such as sulfuric acid, hydrochloric acid, phosphoric acid, nitric acid, p-toluenesulfonic acid, methanesulfonic acid, ethanesulfonic acid, propanesulfonic acid, butanesulfonic acid, an alkylsulfuric acid, or the like, a metal salt such as aluminum lactate, lithium fluoride, potassium chloride, cesium chloride, calcium chloride, iron chloride, aluminum phosphate, or the like, a metal oxide such as a heteropoly acid or the like, a natural/synthetic zeolite, a cation/anion exchange resin, and an organic metal such as a tetraalkyl titanate and a polymer thereof, or the like. As a specific example, tetraalkyl titanate may be used as the catalyst.

A usage amount of the catalyst may vary depending on a type thereof. For example, a homogeneous catalyst may be used at a content of 0.01 to 5 wt %, 0.01 to 3 wt %, 1 to 5 wt %, or 2 to 4 wt % with respect to 100 wt % of the total reactants, and a heterogeneous catalyst may be used at a content of 5 to 200 wt %, 5 to 100 wt %, 20 to 200 wt %, or 20 to 150 wt % with respect to the total weight of the reactants.

The direct esterification is performed at a temperature of 80 to 270° C., preferably 150 to 250° C. for 10 minutes to 10 hours, preferably 30 minutes to 8 hours, and more preferably 1 to 6 hours.

Carboxylic Acid Ester-Based Material in Preparation Process

A case in which each of the carboxylic acid ester-based material including one or more compounds represented by Chemical Formula 5 and the alcohol is one type will be described as an example.

In a process of preparing a plasticizer composition through direct esterification of an acid mixture with an alcohol, an unreacted alcohol not involved in the esterification is volatilized during the reaction due to a high reaction temperature, and the alcohol thus volatilized is condensed and thus added again into the reaction. In this case, a large amount of energy is consumed in a process of recovering and refluxing the volatilized alcohol, which is a factor that may affect a reaction rate.

According to an embodiment of the present invention, it can be suggested that the addition of the carboxylic acid may play a beneficial role in the reaction process.

Specifically, the carboxylic acid ester-based material derived from the carboxylic acid may be present in the reaction process by a reaction with an alcohol involved in the reaction or an optional addition thereof. By including such a carboxylic acid material, more accurately, a carboxylic acid ester-based material, a reaction rate further increases, a temperature rising rate for refluxing also increases, and an amount of alcohol volatilized during heating for refluxing is also reduced so that an effect of saving energy may also be exhibited.

More specifically, in the reaction process, a carboxylic acid ester-based material may be continuously concentrated in a reactor by continuously adding a carboxylic acid, and the absolute amount of alcohol added into the reaction decreases unless the amount of alcohol is optionally increased.

There is a concern that a reaction rate may be lowered due to a decrease in an equivalent ratio of an alcohol involved in esterification caused by a decrease in the absolute amount of alcohol, but an acid and an alcohol may be produced due to an equilibrium reaction (dissociation reaction) of a carboxylic acid ester-based material regardless of a decrease in the absolute amount of alcohol. In this case, the alcohol produced through the equilibrium reaction may result in an effect equivalent to an increase in the content of alcohol through a compensation effect of the relative amount of alcohol involved in the reaction. Also, the acid produced through the equilibrium reaction may partially serve as a catalyst in esterification, and thus a reaction rate may rather increase.

In addition, in the reaction process, the carboxylic acid ester-based material has a boiling point higher than that of an alcohol, and thus is not easily volatilized and remains in a reactor when a temperature rises to a reaction temperature, and the remaining carboxylic acid ester-based material exhibits an effect of increasing reactivity through the above-described action. Also, an amount of alcohol required to reflux when a temperature rises to a reaction temperature may be decreased due to the small absolute amount of alcohol, and a temperature rising rate may also increase due to such a complicated effect.

More specifically, the process of preparing an ester compound may be roughly divided into a reaction process and a purification process. In the purification process, only the product is separated and several batches to several hundred batches of the reaction raw materials including an unreacted alcohol are reused continuously.

As the reaction proceeds, as described above, a carboxylic acid ester-based material may be concentrated in a reactor, and the carboxylic acid ester-based material thus concentrated is recovered and reused together with an alcohol. Also, when a constant amount of the total material including the alcohol and the carboxylic acid ester-based material thus recovered is added to the reaction, an amount of alcohol additionally added is continuously decreased compared to a reaction equivalent ratio due to concentration of the carboxylic acid ester-based material. Generally, when an amount of alcohol additionally added is decreased, a reaction rate may decrease, but an effect equivalent to adding an excessive amount of alcohol may be exhibited due to the action of a carboxylic acid ester derived from a carboxylic acid which is added together with an alcohol or a carboxylic acid ester which is added at an early stage of the reaction.

In addition, energy may be reduced by decreasing an amount of alcohol volatilized and thus a temperature rising rate relatively increases, but a reaction rate may be lowered. The presence of a carboxylic acid ester-based material may exhibit an effect equivalent to adding an excessive amount of alcohol, an effect of assisting a reaction through a dissociation reaction, and the like, and thus may have an advantage of maintaining or increasing a reaction rate.

To more suitably apply the mechanism, the carboxylic acid ester-based material preferably has a boiling point higher than that of an alcohol, and a difference in boiling point is preferably about 30° C. or less.

When $R_{1a}$ in Chemical Formula 5 has 3 or more carbon atoms or a double bond, and thus a difference in boiling point from an alcohol which is a compound represented by Chemical Formula 3 is greatly increased, the separation in the purification process is not performed together with an alcohol, and therefore, an additional separation process may be required.

In addition, the carboxylic acid ester-based material may be included in an amount of preferably 11 parts by weight or less, more preferably 8 parts by weight or less with respect of 100 parts by weight of the dibenzoic acid. When the carboxylic acid ester-based material is included in an amount of greater than 11 parts by weight, a reaction rate may be rather lowered.

In some cases, a propionate may be used as the acetate, which may be determined depending on a difference in boiling point. Also, even when a mixed alcohol is used in esterification, if the mixed alcohol is a material which can be smoothly separated from a product in the purification process, the above-described effect may be exhibited.

Resin Composition

According to another embodiment of the present invention, the composition prepared by the above-described method of preparing an ester-based composition may be applied as a plasticizer, and there is provided a resin composition including the plasticizer and a resin.

The resin may be a resin known in the related art. For example, a mixture of one or more selected from ethylene vinyl acetate, polyethylene, polypropylene, polyvinyl chloride, polyketone, polystyrene, polyurethane, a thermoplastic elastomer, and polylactic acid may be used as the resin, but the present invention is not limited thereto.

The plasticizer composition may be included in an amount of 5 to 150 parts by weight with respect to 100 parts by weight of the resin.

The resin composition may further include a filler. The filler may be included in an amount of 0 to 300 parts by weight, preferably 50 to 200 parts by weight, and more preferably 100 to 200 parts by weight with respect to 100 parts by weight of the resin.

The filler may be a filler known in the related art, but the present invention is not limited. For example, a mixture of one or more selected from silica, magnesium carbonate, calcium carbonate, hard charcoal, talc, magnesium hydroxide, titanium dioxide, magnesium oxide, calcium hydroxide, aluminum hydroxide, aluminum silicate, magnesium silicate, and barium sulfate may be used as the filler.

In addition, the resin composition may further include other additives such as a stabilizer and the like as necessary. The additives such as a stabilizer and the like may be included, for example, in an amount of 0 to 20 parts by weight, preferably 1 to 15 parts by weight with respect to 100 parts by weight of the resin.

For example, a calcium-zinc (Ca—Zn)-based stabilizer such as calcium-zinc combined stearate or the like may be used as the stabilizer, but the present invention is not particularly limited thereto.

The plasticizer composition thus prepared is included in an amount of 5 to 150 parts by weight, 40 to 100 parts by weight, or 40 to 50 parts by weight with respect to 100 parts by weight of a resin selected from ethylene vinyl acetate, polyethylene, polypropylene, polyvinyl chloride, polystyrene, polyurethane, and a thermoplastic elastomer, and thus a resin composition which is effective in all of compound formulation, sheet formulation, and plastisol formulation may be provided. For example, the plasticizer composition may be applied in the fabrication of electric wires, flooring materials, interior materials for automobiles, films, sheets, wallpaper, or tubes.

EXAMPLES

Hereinafter, embodiments will be described in detail for promoting an understanding of the present invention. However, embodiments of the present invention may be modified in several different forms, and the scope of the present invention is not limited to the embodiments to be described below. The embodiments of the present invention are provided so that this disclosure will be thorough and complete, and will fully convey the concept of embodiments to those skilled in the art.

Examples 1 to 5

Terephthalic acid as a dibenzoic acid and acetic acid as a carboxylic acid were mixed to prepare an acid mixture, and 2-ethylhexanol as an alcohol was added to the acid mixture. The acid mixture and 2-ethylhexanol were subjected to esterification, and then Examples 1 to 5 were set in accordance with the contents of 2-ethylhexyl acetate as listed in Table 1 below.

Reference Example 1

A reaction was performed in the same manner as in Examples 1 to 3, but it was performed after acetic acid was completely removed, and a case, in which the content of acetate produced was 0, was set as a reference example.

TABLE 1

| No. | Content of 2-ethylhexyl acetate (parts by weight)* | Total amount of 2-ethylhexanol refluxed (kg) | Excessive amount of 2-ethylhexanol |
|---|---|---|---|
| Reference Example 1 | 0 | 4,590 kg | 5,200 kg |
| Example 1 | 3.85 | 3,860 kg | 5,000 kg |
| Example 2 | 5.76 | 3,480 kg | 4,900 kg |
| Example 3 | 7.68 | 3,050 kg | 4,800 kg |
| Example 4 | 11.5 | 2,760 kg | 4,600 kg |
| Example 5 | 23.0 | 2,450 kg | 4,000 kg |

*based on 100 parts by weight of terephthalic acid

Experimental Example 1: Measurement of Reaction Rate

For Examples 1 to 5 and Reference Example 1, an esterification reaction rate was measured, a result of which is shown in FIG. 1.

In the preparation of a terephthalate material, a point in time when a reaction is terminated is generally based on an acid value. When an acid value when a reaction is terminated was set to 0.5, referring to FIG. 1, it can be confirmed that Examples 1 to 3, in which the contents of 2-ethylhexyl acetate were 8 parts by weight or less, exhibited the same level of high reaction rate as in Reference Example 1, and Examples 4 and 5, in which the contents thereof were greater than 11 parts by weight, rather exhibited a decreased reaction rate. From these results, it can be confirmed that, when a specific amount of 2-ethylhexyl acetate derived from acetic acid was included, a reaction rate was not affected.

This indicates that when a predetermined amount of 2-ethylhexyl acetate is included in a reaction composition, a reaction rate is not adversely affected, but when an amount thereof is increased by a predetermined amount or more, a reaction rate is significantly lowered when the total addition amount including an alcohol and an acetate is based on the same weight.

In addition, it can be indirectly seen that energy is significantly consumed due to a large amount of alcohol refluxed in the case of Reference Example 1 not including 2-ethylhexyl acetate.

Example 6 and Reference Examples 2 and 3

Terephthalic acid as a dibenzoic acid and acetic acid as a carboxylic acid were mixed to prepare an acid mixture, 2-ethylhexanol as an alcohol was added to the acid mixture, and then the acid mixture and 2-ethylhexanol were subjected to esterification. In accordance with the addition of an excessive amount of alcohol and the content of 2-ethylhexyl acetate, a case in which an excessive amount of 2-ethylhexanol was included at 50% was set as Reference Example 2, a case in which an excessive amount of 2-ethylhexanol was included at only 35% was set as Reference Example 3 for comparison, and a case in which an excessive amount of 2-ethylhexanol was included at 35% and 2-ethylhexyl acetate was included at 15% instead of 2-ethylhexanol was set as Example 6. Also, each temperature rising rate was measured, a result of which is shown in FIG. 2.

Experimental Example 2: Measurement of Temperature Rising Rate

Figure 2:
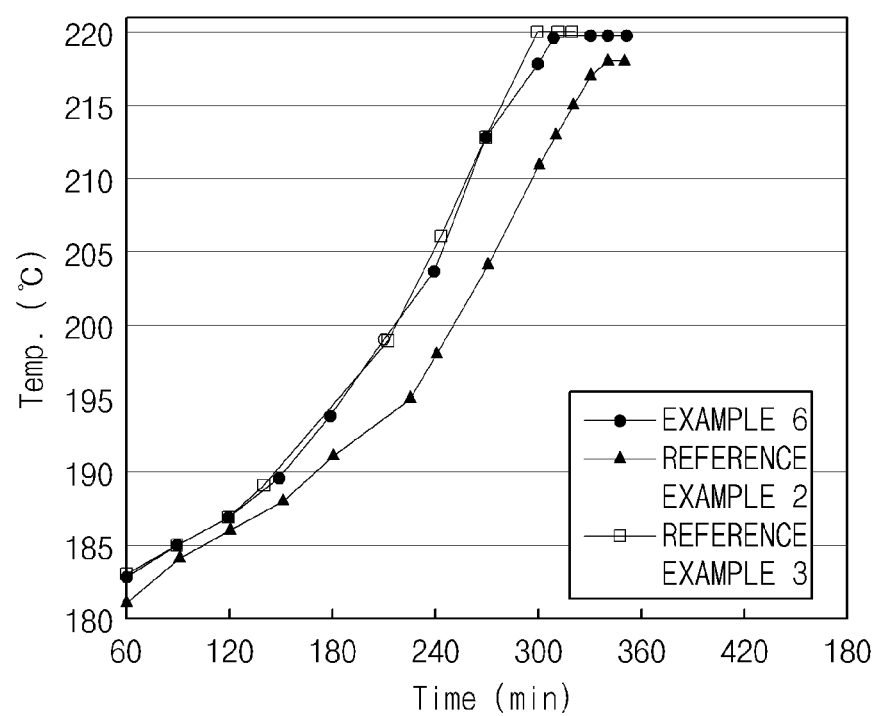
FIG. 2 is a graph obtained by measuring a temperature rising rate until reaching a reaction temperature during esterification.

For Example 6 and Reference Examples 2 and 3, a temperature rising rate during esterification was measured, a result of which is shown in FIG. 2.

FIG. 2 illustrates a result of measuring the extent to which a temperature rises over time. Referring to FIG. 2, it can be seen that, Reference Examples 2 and 3 not including acetic acid exhibited a difference in a temperature rising rate in accordance with an excessive amount of 2-ethylhexanol, which confirms that a temperature rising rate decreased when an excessive amount of 2-ethylhexanol was large because a relatively and absolute large amount of alcohol was volatilized when a temperature had risen to a reaction temperature of about 220° C. Also, it can be confirmed that Example 6 including 2-ethylhexyl acetate exhibited a temperature rising rate equivalent to a case not including acetic acid, which is due to the presence of acetic acid even though an absolute large amount of alcohol is volatilized. Also, on the basis of the same amount, it can be confirmed that a temperature rising rate was further improved in a case including 2-ethylhexyl acetate.

Furthermore, in consideration of Experimental Examples 1 and 2 and FIGS. 1 and 2, it can be seen that when a small amount of 2-ethylhexanol is additionally added, a temperature rising rate increases, but a reaction rate decreases so that a reaction time is delayed (due to a decrease in an absolute amount), and when 2-ethylhexyl acetate is concentrated during the process and thus participates with 2-ethylhexanol in the reaction, a temperature rising rate increases and a reaction rate also increases so that a reaction time is shortened (due to effects of decreasing an amount of 2-ethylhexanol volatilized and assisting a reaction through a dissociation (equilibrium) reaction). Also, when 2-ethylhexyl acetate is involved in the reaction, an amount of alcohol refluxed is relatively decreased, which results in an effect of reducing energy that is consumed during the process.

While exemplary embodiments have been described above in detail, the scope of the present invention is not limited thereto, but encompasses several modifications and improvements by those skilled in the art using basic concepts of embodiments of the present invention defined by the appended claims.

The invention claimed is:

1. A method of preparing an ester-based composition, the method comprising:

reacting a) a dibenzoic acid represented by Chemical Formula 1; b) one or more selected from the group consisting of a carboxylic acid represented by Chemical Formula 2 and a carboxylic acid ester-based material including one or more compounds represented by Chemical Formula 5; and c) an alcohol including one or more compounds represented by Chemical Formula 3, wherein a product of the reaction includes a benzoic acid ester-based material including one or more compounds represented by Chemical Formula 4 and a carboxylic acid ester-based material including one or more compounds represented by Chemical Formula 5 wherein the carboxylic acid ester-based material including one or more compounds represented by Chemical Formula 5 in the product of the reaction is included at 11 parts by weight or less with respect to 100 parts by weight of the dibenzoic acid represented by Chemical Formula 1:

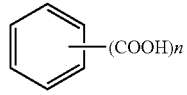  [Chemical Formula 1]

wherein n is 2,

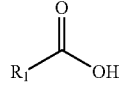  [Chemical Formula 2]

wherein $R_1$ is a C1 or C2 alkyl group, $R_2$—OH  [Chemical Formula 3]

wherein $R_2$ is a C1 to C12 linear alkyl group or a C3 to C12 branched alkyl group,

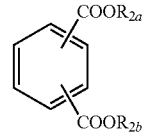  [Chemical Formula 4]

wherein $R_{2a}$ and $R_{2b}$ are the same or different from each other, and each independently are a linear alkyl group or a C3 to C12 branched alkyl group,

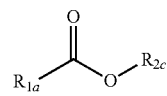  [Chemical Formula 5]

wherein $R_{1a}$ is a C1 or C2 alkyl group, and $R_{2c}$ is a C1 to C12 linear alkyl group or a C3 to C12 branched alkyl group.

2. The method of claim 1, wherein $R_2$, $R_{2a}$, $R_{2b}$, and $R_{2c}$ in Chemical Formulas 3 to 5 are C4 to C10 linear or branched alkyl groups.

3. The method of claim 1, wherein $R_{2a}$, $R_{2b}$, and $R_{2c}$ in Chemical Formulas 4 and 5 are alkyl groups derived from $R_2$ in Chemical Formula 3.

4. The method of claim 1, wherein $R_{2c}$ in Chemical Formula 5 is the same as $R_2$ in Chemical Formula 3.

5. A method of preparing a plasticizer composition comprising:

preparing an ester-based composition according to the method of claim 1; and purifying the ester-based composition.

* * * * *